United States Patent [19]

Wheatley et al.

[11] Patent Number: 5,352,436
[45] Date of Patent: Oct. 4, 1994

[54] SURFACTANT-STABILIZED MICROBUBBLE MIXTURES, PROCESS FOR PREPARING AND METHODS OF USING THE SAME

[75] Inventors: Margaret A. Wheatley, Media, Pa.; Shen Peng, Hayward, Calif.; Shruti Singhal, Penn Valley; Barry B. Goldberg, Oreland, both of Pa.

[73] Assignee: Drexel University, Philadelphia, Pa.

[21] Appl. No.: 162,421

[22] Filed: Nov. 22, 1993

Related U.S. Application Data

[63] Continuation of Ser. No. 970,343, Nov. 2, 1992, abandoned.

[51] Int. Cl.$^5$ .............................................. A61K 49/00
[52] U.S. Cl. .................................... 424/9; 128/660.02
[58] Field of Search ......................... 424/9; 128/660.02

[56] References Cited

U.S. PATENT DOCUMENTS

| | | | |
|---|---|---|---|
| 4,466,442 | 8/1984 | Hilmann et al. | 128/653 |
| 4,615,879 | 10/1986 | Runge et al. | 424/9 |
| 4,684,479 | 8/1987 | D'Arrigo | 252/307 |
| 4,764,574 | 8/1988 | Clark, Jr. | 526/207 |
| 4,774,958 | 10/1988 | Feinstein | 424/2 |
| 4,832,941 | 5/1989 | Berwing et al. | 424/9 |
| 4,844,882 | 7/1989 | Widder et al. | 424/9 |
| 4,957,656 | 9/1990 | Cerny et al. | 424/9 |

OTHER PUBLICATIONS

H. J. Bleeker, K. K. Shung and J. L. Barnhart, "Ultrasonic Characterization of Albunex ®, a New Contrast Agent," *J. Acoust. Soc. Am.* 87(4), Apr. 1990, pp. 1792–1797.

N. Nanda (E. D.), "Advances in EchoContrast Enhancement," *Advances in EchoContrast (Aims and Scope)*, 1989.

*Primary Examiner*—Richard L. Raymond
*Attorney, Agent, or Firm*—Panitch Schwarze Jacobs & Nadel

[57] ABSTRACT

The present invention is a mixture including a solvent, a first surfactant and a second, dispersible surfactant different from the first surfactant, the mixture having stabilized gas microbubbles formed therein by sonication. The gas microbubbles are useful in ultrasonic diagnostics. Preferably the first surfactant is substantially soluble in the solvent and the second surfactant is substantially insoluble in the solvent. The present invention also includes a process for preparing the stabilized gas microbubbles and a method for altering the contrast of an ultrasonic image using the microbubbles as a contrast agent.

26 Claims, 2 Drawing Sheets

SURFACTANT-STABILIZED MICROBUBBLE MIXTURES, PROCESS FOR PREPARING AND METHODS OF USING THE SAME

STATEMENT OF GOVERNMENT INTEREST

This invention was made in part with Government support under Research Grant No. CA52823 awarded by the National Institutes of Health. The Government may have certain rights in this invention.

This is a continuation of application Ser. No. 07/970,343, filed Nov. 2, 1992, now abandoned.

FIELD OF THE INVENTION

The present invention relates to a mixture having stabilized gas microbubbles formed therein by sonication and a process for making and methods for using the same. More particularly, the invention is directed to formation of stabilized gas microbubbles for use as contrast agents for ultrasonic diagnostics.

BACKGROUND OF THE INVENTION

Stabilized gas-in-liquid emulsions are useful in a variety of fields, such as food technology, marine biology, hydraulic and ocean engineering and echocardiography, to name a few. Gas microbubbles are particularly useful as contrast agents for ultrasonic diagnostics of fluid-filled human and animal body cavities and organs. In ultrasonic diagnostics, contrast agents provide better contrast resolution between normal and diseased cavities; outline vessels; characterize tissue; enhance Doppler signals in blood flow measurements; and are useful in dynamic studies, for example, to measure the rate of uptake and/or clearance of an agent in a specific location of the body. Contrast agents are particularly useful in echocardiography since injected air microbubbles travel with intracardiac velocities similar to red blood cells. Such microbubbles permit monitoring of blood flow which shows changes both in tumor neovascularization and in normal vascularization patterns of organs neighboring abdominal masses. This can provide earlier diagnosis of these abdominal masses.

There are three potential theoretical mechanisms for enhancing an ultrasound image, namely, increasing sonic backscatter, increasing the rate of attenuation of sound energy and altering the speed of transmission of ultrasound waves. Conventional ultrasound devices rely on generation of an image from backscattered ultrasound radiation. The term "echogenicity" refers to the degree of enhancement of backscatter. The echogenicity of an ultrasound contrast agent depends on experimental conditions and differences in physical properties of the scatterer and the suspending medium. Sonic backscatter may be increased by including free gas bubbles in a suspending medium. However, such free gas bubbles are short-lived and are quickly and completely removed by the lungs.

Typical prior art contrast mediums include encapsulated gas bubbles that exhibit better stability than free gas bubbles. However, such prior art encapsulated gas bubbles generally have a mean diameter greater than 10 μm and can become entrapped in the capillary bed of the lung. Conventional microbubbles have been encapsulated in gelatin and albumen, for example. AL-BUNEX®, which has been developed by Molecular Biosystems, Inc. of San Diego, Calif., is a suspension of stable microencapsulated air bubbles of a size ranging from 0.5 to 10 μm. The air bubbles are produced by sonication of a 5% human serum albumin solution. The gas bubbles are encapsulated in a coagulated protein shell. The microcapsules tend to be rather fragile in nature, and encounter problems in the high pressure environment of the chambers of the heart.

One agent which has been used to generate microbubbles is a sugar molecular matrix (SHU-454 and SHU-508), which is supplied as a crystalline solid by Schering AG (West Germany). Microbubbles are liberated from the matrix by addition of a sterile buffer solution just prior to administration, and range in size from 1 to 5 μm.

U.S. Pat. No. 4,684,479 discloses surfactant mixtures for the production of stable gas-in-liquid emulsions comprising: (a) a glycerol monoester of saturated carboxylic acids containing from about 10 to about 18 carbon atoms or aliphatic alcohols containing from about 10 to about 18 carbon atoms; (b) a sterol-aromatic acid ester; and (c) a sterol, terpene, bile acid or alkali metal salt of a bile acid. Optionally, the mixture may also include various sterol esters, esters of sugar acids and aliphatic alcohols, sugar acids, saponins, sapogenins and glycerols.

U.S. Pat. No. 4,466,442 discloses a solution for the production of gas microbubbles which contains a solution of at least one tenside and at least one viscosity-raising compound. Examples of suitable non-ionic tensides include polyoxyethylene fatty acid esters, and polyoxyethylated sorbitan fatty acid esters. Examples of viscosity-raising compounds include mono- or polysaccharides, dextrans, cyclodextrins, hydroxyethyl amylose, polyols, proteins, proteinaceous materials, amino acids and blood surrogates.

Desirable contrast agents improve resolution for imaging of cardiac, solid organ and vascular anatomic conduits (including agent localization, for example due to macrophage activity); solid organ perfusion; and Doppler signals of blood velocity and flow direction during real time imaging. For an ultrasound contrast agent to be effective, it must be stable, biocompatible, and must provide improved acoustic echoes from tissue with relatively low toxicity.

It is desirable to have an ultrasound contrast agent comprising microbubbles having a mean average diameter less than 10 μm which are stable not only in storage but are also stable for at least one pass inside a human or animal subject and which exhibit a high degree of echogenicity under all modes of medical ultrasound imaging.

BRIEF SUMMARY OF THE INVENTION

According to the present invention, a mixture is provided which has stabilized gas microbubbles formed therein by sonication. The gas microbubbles are for use in ultrasonic diagnostics. The mixture comprises a solvent, a first surfactant and a second, dispersible surfactant.

Another aspect of the present invention is a process for preparing stabilized gas microbubbles for use in ultrasonic diagnostics. The process comprises mixing a solvent, a first surfactant and a second, dispersible surfactant. Microbubbles are generated in the mixture by exposing the mixture to ultrasound sonication. The microbubbles generated by the ultrasound sonication are collected by separating at least a portion of the solvent from the microbubbles.

Another aspect of the present invention is a method for altering the contrast of an ultrasonic image. The method comprises forming a mixture of a solvent, a first surfactant and a second, dispersible surfactant. The mixture has stabilized gas microbubbles formed therein by sonication. The microbubbles are collected by separating at least a portion of the solvent from the microbubbles. The microbubbles are intravenously injected into a body to substantially alter the contrast of an ultrasonic image of a portion of the body containing the microbubbles therein.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments of the invention, it being understood, however, that the invention is not limited to the specific methods and embodiments disclosed. In the drawings.

DESCRIPTION OF THE PREFERRED EMBODIMENTS

Figure 1:
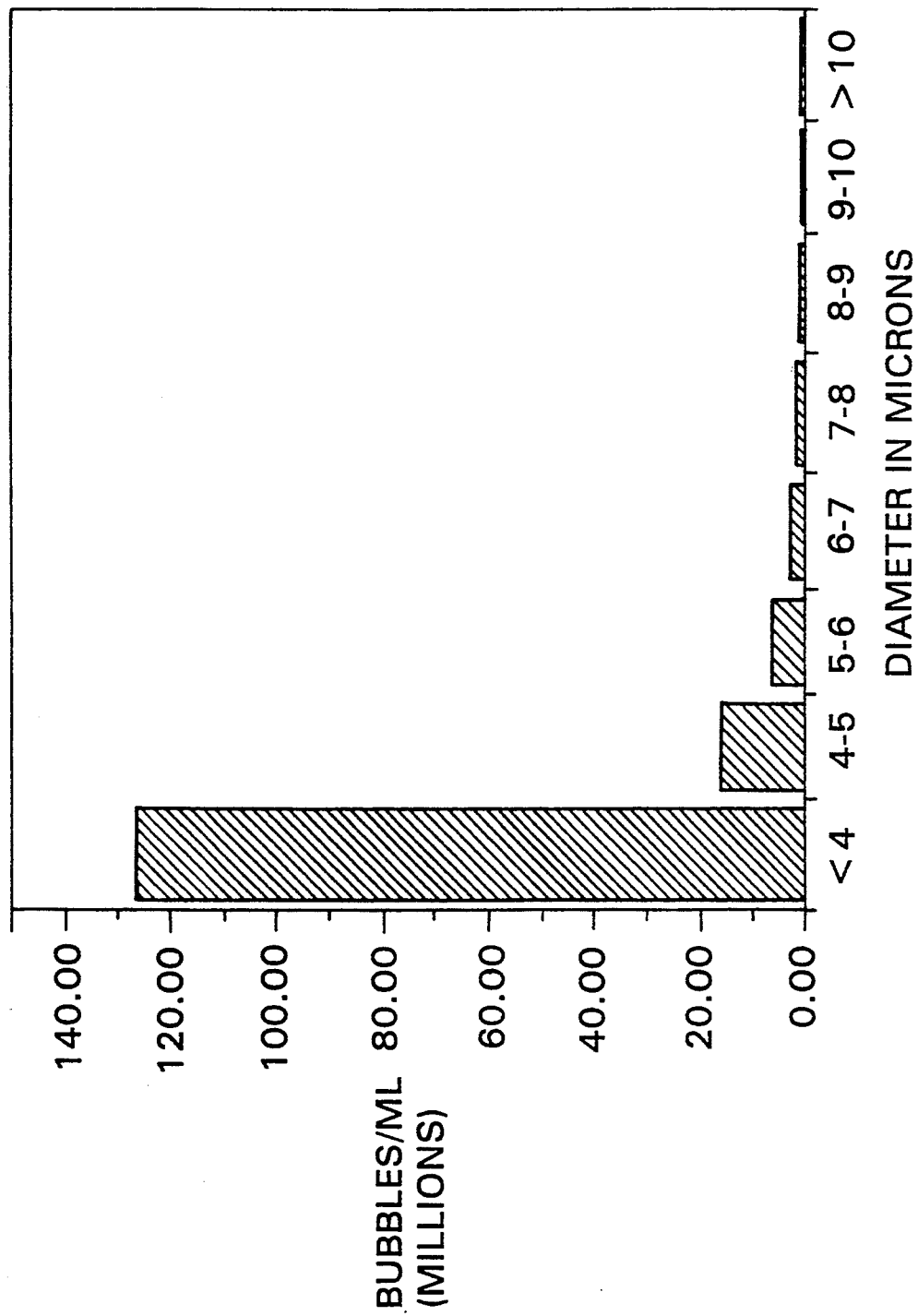
FIG. 1 is a graph of millions of microbubbles per ml of collected microbubble phase of the mixture as a function of mean bubble diameter in microns.

The stabilized gas microbubbles of the present invention are formed by sonication of a mixture comprising a solvent, a first surfactant and a second, dispersible surfactant.

The mixture includes a solvent, such as an aqueous solution. Suitable solvents include water, saline or any suitable salt solution in accordance with the present invention. Preferably, the solvent is a phosphate buffered saline solution having a pH ranging from about 7.0 to about 7.5 and, more preferably, ranging from about 7.2 to about 7.4. A preferred phosphate buffered saline solution has dissolved solids of about 86% sodium chloride, about 10% sodium phosphate, about 2% potassium chloride and about 2% potassium dihydrogen phosphate. In a preferred embodiment, additional sodium chloride is added to the saline solution to facilitate dispersion of the surfactant and enhance the stability of the resulting microbubble preparation.

The ratio of solvent to the soluble surfactant is about 100:1 to about 20:1 by weight. The ratio of solvent to the insoluble surfactant is about 100:1 to about 25:1 by weight.

Preferably, the first surfactant is substantially soluble in the solvent, although one of ordinary skill in the art would understand that partially soluble or insoluble surfactants may also be useful in the present invention as the first surfactant. It is further preferred that the first surfactant be non-ionic. Suitable first surfactants include polyoxyethylene fatty acid esters, such as polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate and mixtures thereof.

Suitable polyoxyethylene fatty acid esters include TWEEN 20, TWEEN 40, TWEEN 60, TWEEN 65 and TWEEN 80, each of which are commercially available from ICI Americas, Inc. of Wilmington, Del. The TWEEN surfactants are each mixtures of various polyoxyethylene fatty acid esters in liquid form. For example, TWEEN 20 comprises polyoxyethylene (POE) esters of about 60 weight percent lauric acid (dodecanoic acid); about 18% myristic acid (tetradecanoic acid); about 7% caprylic acid (octanoic acid) and about 6% capric acid (decanoic acid). TWEEN 40 generally comprises POE esters of about 90% palmitic acid (hexadecanoic acid). TWEEN 60 generally comprises POE esters of about 49% stearic acid (octadecanoic acid) and about 44% palmitic acid. TWEEN 80 generally comprises POE esters of about 69% oleic acid (cis-9-octadecanoic acid); about 3% linoleic acid (linolic acid); about 3% linolenic acid (9,12,15-octadecatrienoic acid); about 1% stearic acid and about 1% palmitic acid.

The second, dispersible surfactant is different from the first surfactant. Preferably the second, dispersible surfactant is insoluble, although one of ordinary skill in the art would understand that the second surfactant may be partially or fully soluble in the solvent. It is further preferred that the second surfactant is non-ionic. Suitable second surfactants include sorbitan fatty acid esters, such as sorbitan monostearate, sorbitan monopalmitate and mixtures thereof. Preferred mixtures of sorbitan fatty esters include SPAN 40 and SPAN 60, each of which are dry powders commercially available from ICI Americas, Inc. SPAN 40 comprises sorbitan esters of about 93% palmitic acid; about 2.5% myristic acid and less than about 1% pentadecanoic acid. SPAN 60 comprises sorbitan esters of about 50% stearic acid, about 45% palmitic acid and about 2% myristic acid.

Preferably, the molar ratio of first surfactant to second surfactant is about 1:1.7. One of ordinary skill in the art would understand that the ratio of first surfactant to second surfactant may vary based upon such factors as the particular first surfactant and second surfactant selected. By way of example, the ratio of first surfactant to second, dispersible surfactant for mixtures TWEEN 20, TWEEN 40, TWEEN 60, TWEEN 65 or TWEEN 80 and SPAN 40 or SPAN 60 is about 1:0.5 by weight to about 1:1.5 by weight.

The stabilized gas microbubbles may be prepared from the mixture by a variety of methods. Generally, microbubbles are formed by mixing the first surfactant and second, dispersible surfactant with the solvent to form a mixture and then exposing the mixture to ultrasound sonication to generate the microbubbles.

The first surfactant, second surfactant and solvent may be mixed by a variety of methods well known to those of ordinary skill in the art. Examples of methods for mixing these components are set forth in Examples 1 and 2 below. Each of these examples are merely for purposes of illustration and are not intended to be limiting.

EXAMPLE 1

In a preferred method for making the surfactant stabilized microbubbles, about 4.0 grams of sodium chloride is dissolved in 50 ml of phosphate buffered saline solution to form a diluent having a pH of about 7.2. About 1.0 grams of SPAN 60 is added to the diluent and the resulting mixture is stirred for about 1.5 to about 2 hours at room temperature (about 25°). About 1 ml of TWEEN 80 is added to this mixture and stirred for about 10 to about 15 minutes.

EXAMPLE 2

In an alternative embodiment, about 1 g of sodium chloride is intimately mixed with 1 g of SPAN 40 powder by crushing the mixture and dispersed in about 10 ml of phosphate buffered saline solution. The solution is diluted in about 40 ml of phosphate buffered saline solution. About 1 ml of TWEEN 40 is added to the diluted solution and stirred vigorously at room temperature (about 25° C.) for about 15 minutes.

Generally, the microbubbles are generated by exposing the mixture to ultrasound sonication for about 1 to about 3 minutes. A suitable ultrasound device for generating microbubbles is commercially available from Heat Systems Ultrasonics, Inc. of Farmingdale, N.Y. as Model W385, having a one quarter inch diameter sonicator probe attached thereto. Other suitable ultrasonic devices are commercially available from Branson Ultrasonics Corp. of Danbury, Conn. and Crest Ultrasonics, of Trenton, N.J., for example. Suitable ultrasound power levels for generating the microbubbles are between about 140 to 200 watts. Preferably, the mixture is sonicated for three minutes at a power level of 140 watts. The microbubbles are generated from dissolved air in the mixture by cavitation caused by the ultrasound sonication of the mixture. One of ordinary skill in the art would understand that the microbubbles may be formed from other gases, such as nitrogen, which may be included in the mixture.

To separate the microbubbles from the sonicated mixture, the mixture may be placed in a separating apparatus, such as a separatory funnel. The mixture is permitted to separate into a dense solvent layer or aqueous lower phase, an intermediate layer or less dense phase comprising substantially all of the microbubbles having a mean diameter less than about 10 $\mu$m and an upper layer comprising substantially all of the bubbles having a mean diameter greater than about 10 $\mu$m. The intermediate layer is separated from substantially all of the upper layer and the lower layer. The concentration of the microbubbles in the microbubble phase may be adjusted based upon the quantity of solvent or lower layer separated from the microbubble phase. The concentration of microbubbles in the microbubble phase after separation and collection generally ranges from about $1 \times 10^7$ to about $1 \times 10^{10}$ bubbles per ml of microbubble phase.

The microbubbles are washed with a saline solution, such as the phosphate buffered saline solution discussed above. Preferably, the microbubbles are washed by spraying with about 10 to about 15 mls of the phosphate buffered saline solution. The microbubbles and wash mixture may again be separated by gravity to collect the layer of surfactant-stabilized microbubbles above the solvent or lower layer. Microbubbles made in accordance with the present invention remain generally stable for about three days at room temperature (about 25° C.) in a phosphate buffered saline solution. Alternatively, the mixture may be cooled to about 4° C. to prolong the stability of the microbubbles.

The mean particle diameter of the stabilized microbubbles generated is preferably less than about 10 $\mu$m. As shown in FIG. 1, 99.49% of the microbubbles generated from a 1:1 mixture of SPAN 60 and of TWEEN 80, according to the method set forth in Example 2, had a mean particle diameter less than about 10 $\mu$m, with about 80.82% of the microbubbles having a mean diameter less than about 4 $\mu$m. The mean particle diameter was 3.59 $\mu$m.

Another aspect of the present invention is a method for enhancing the contrast of an ultrasonic image using the surfactant-stabilized microbubbles of the present invention. The microbubbles may be intravenously or intra-arterially, for example, injected into the body of a human or animal, for example, to substantially alter the contrast of an ultrasonic image of a portion of the body containing the microbubbles therein. The microbubbles may be substantially evenly distributed in a saline solution, such as a phosphate buffered saline solution, prior to injecting the microbubbles into the body.

The present invention will now be illustrated in more detail by reference to the following specific, non-limiting examples:

EXAMPLE A

Figure 2:
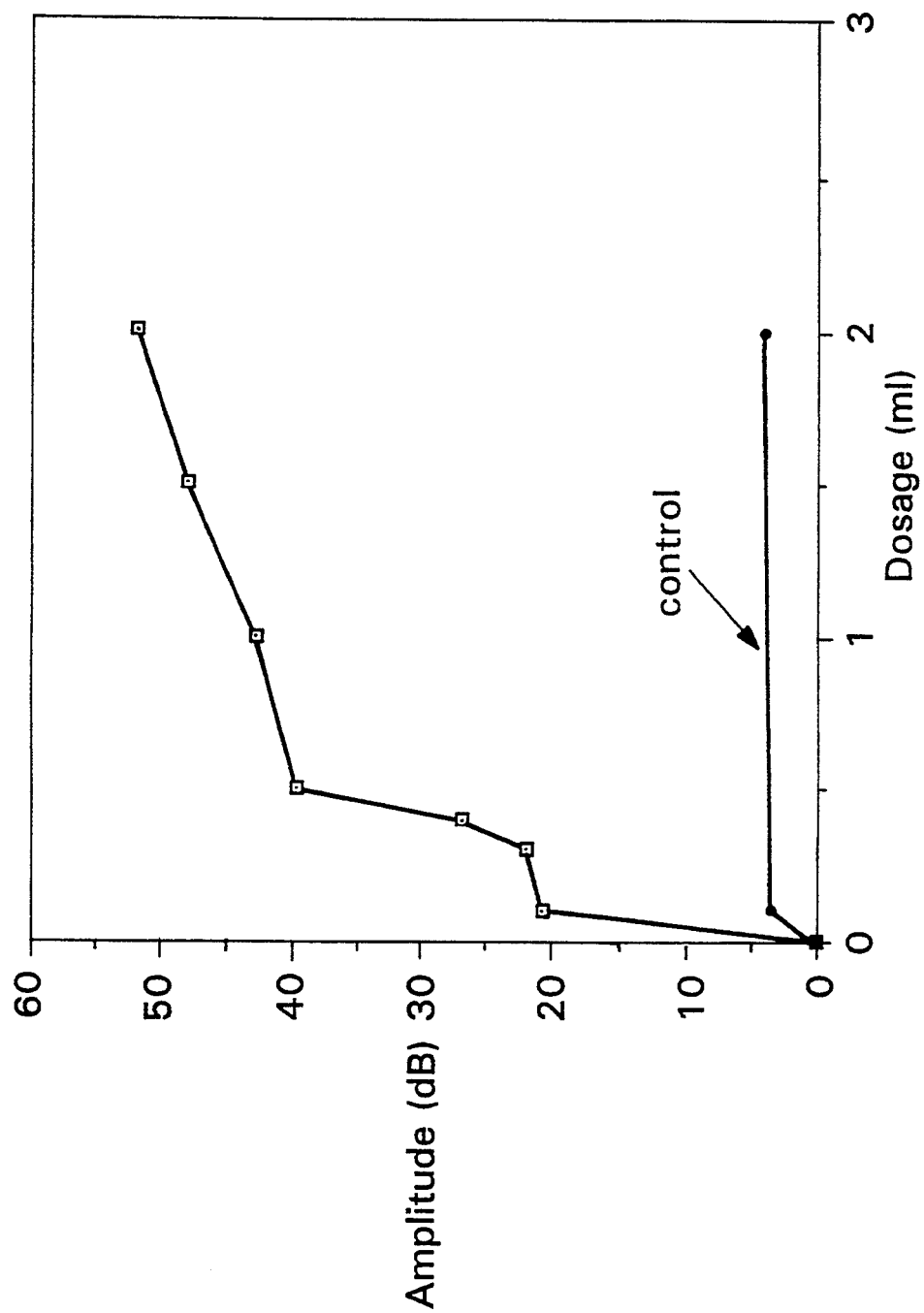
FIG. 2 is a graph of amplitude (dB) of Doppler spectral image as a function of dosage of microbubble mixture injected in ml.

A sedated woodchuck was catheterized in the jugular vein to permit injection of the microbubble mixture. The microbubbles were generated from a mixture of phosphate buffered saline solution, 1.0 g of SPAN 60 and 1.0 ml of TWEEN 80 according to the method of Example 2. The concentration of microbubbles in the mixture was $1.58 \times 10^8$ particles/ml and the microbubbles in the mixture had a mean particle size of 3.59 $\mu$m. The temperature of the microbubble mixture prior to injection was about 25° C. (room temperature). The vial containing the microbubble mixture was gently agitated to ensure even suspension of the bubbles before the mixture was taken up into a syringe through an 18 G needle. For purposes of comparison, the woodchuck was injected with 1 ml of the phosphate buffered saline solution as a control. A series of doses, namely 0.1 ml, 0.2 ml, 1.5 ml and 2.0 ml, of the microbubble mixture was injected into the woodchuck, each being followed by 1 ml of saline solution to flush the microbubble mixture from the injection apparatus. Doppler spectral images were recorded during the woodchuck experiment using a cuff transducer placed around the ceiliac artery of the woodchuck. The recorded Doppler spectral images clearly demonstrated that the microbubbles not only passed the capillary bed of the lung, but also survived the high pressure environment of the left chambers of the heart and were strongly echogenic in a dose-dependent fashion. As shown in FIG. 2, as the dosage of microbubble mixture was increased, the amplitude or intensity of the Doppler spectral image increased. In contrast, the amplitude of the control remained substantially the same as the dosage of control was increased.

EXAMPLE B

Microbubbles were generated from a mixture of phosphate buffered saline solution, 1.0 g of SPAN 40 and 1.0 ml of TWEEN 40 according to the method of Example 2. The collected microbubbles, having a mean bubble diameter of 5.4 $\mu$m, were injected into a New Zealand white rabbit in a similar manner to that set forth above in Example A. The aorta of the rabbit was imaged using a 5 MHz transducer scanning over the skin of the rabbit. The signal was recorded on a tape using a Diasonic Spectra Plus ultrasound system. The signal intensity increased after injection of the surfactant-stabilized microbubbles of the present invention.

EXAMPLE C

A mixture of phosphate buffered saline solution 1.0 g of SPAN 40 and 1.0 ml of TWEEN 40 was prepared according to the method of Example 2. Microbubbles having a mean bubble diameter of 6.4 μm were generated, collected, and injected into the rabbit as set forth above in Example A. Colored Doppler images of the rabbit kidney before and after injection of the agent clearly show the beneficial effect of the surfactant-stabilized microbubble contrast agent of the present invention in enhancing the intensity of the signal.

EXAMPLE D

A woodchuck was obtained from a colony of the Philadelphia Zoo which is naturally infected with a nonhuman hepatitis virus which causes hepatic tumors. The hepatic tumor-bearing woodchuck was sedated and catheterized in the jugular vein to permit injection of the contrast agent of the present invention. The woodchuck was injected with microbubbles formed from a mixture of phosphate buffered saline solution, 1.0 g of SPAN 60 and 1.0 ml of TWEEN 80 mixed according to the method of Example 2. The liver was imaged with a 7.5 MHz transduced scanning over skin of the woodchuck. The resulting color Doppler images of the woodchuck liver prior to and after injection clearly show that the contrast agent of the present invention enhanced the image of the vascular hepatic tumor.

The surfactant-stabilized gas microbubbles of the present invention are more stable than typical prior art hand agitated solutions of gas microbubbles, both in storage and after injection into subjects. The present stabilized gas microbubbles exhibit a high degree of echogenicity under B-mode scan, regular Doppler and color Doppler. The present microbubbles are useful as contrast agents to provide better contrast resolution for ultrasonic diagnostics, including echocardiography.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined in the appended claims.

We claim:

1. A mixture having stabilized gas microbubbles formed therein by sonication, the gas microbubbles having a mean diameter of less than about 10 micrometers, and being for use in ultrasonic diagnostics, comprising
   a substantially aqueous solvent;
   a first surfactant; and
   a second, substantially water-dispersible surfactant different from the first surfactant.

2. A mixture according to claim 1, wherein said first surfactant is substantially soluble in said solvent.

3. A mixture according to claim 1, wherein said first surfactant is non-ionic.

4. A mixture according to claim 1, wherein said first surfactant comprises a polyoxyethylene fatty acid ester.

5. A mixture according to claim 4, wherein said polyoxyethylene fatty acid ester is selected from the group consisting of polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate and mixtures thereof.

6. A mixture according to claim 1, wherein said second surfactant is substantially insoluble in said solvent.

7. A mixture according to claim 1, wherein said second surfactant is non-ionic.

8. A mixture according to claim 1, wherein said second surfactant comprises a sorbitan fatty acid ester.

9. A mixture according to claim 8, wherein said sorbitan fatty acid ester is selected from the group consisting of sorbitan monostearate, sorbitan monopalmitate, and mixtures thereof.

10. A mixture according to claim 1, wherein the ratio of first surfactant to second surfactant is between about 1:0.5 to about 1:1.5 by weight.

11. A mixture according to claim 1, wherein the molar ratio of first surfactant to second surfactant is about 1:1.7.

12. A mixture according to claim 1, wherein the concentration of said microbubbles is between about $1 \times 10^7$ and about $1 \times 10^{10}$ particles/ml of mixture.

13. A mixture according to claim 1, wherein said solvent comprises a saline solution.

14. A mixture according to claim 13, wherein said saline solution is a phosphate saline solution having a pH ranging from about 7.0 to about 7.5.

15. A process for preparing stabilized gas microbubbles having a mean diameter of less than about 10 micrometers, and being for use in ultrasonic diagnostics, comprising the steps of:
   (a) mixing a solvent, a first surfactant and a second, dispersible surfactant to form a mixture, said second surfactant being different from said first surfactant;
   (b) generating microbubbles having a mean diameter of less than about 10 micrometers in said mixture by exposing said mixture to ultrasound sonication;
   (c) collecting said microbubbles by separating at least a portion of said solvent from said microbubbles.

16. A process according to claim 15, wherein said solvent comprises a saline solution to form said mixture.

17. A process according to claim 15, wherein said first surfactant is substantially soluble in said solvent.

18. A process according to claim 15, wherein said second surfactant is substantially insoluble in said solvent.

19. A process according to claim 15, wherein said mixture is exposed to said ultrasound sonication for about 1 to about 3 minutes.

20. A process according to claim 15, wherein the step of generating microbubbles further comprises permitting said microbubbles to form an intermediate layer comprising microbubbles, each microbubble having a diameter less than about 10 μm, said intermediate layer being located between a lower layer which substantially comprises said solvent and an upper layer which substantially comprises bubbles having a diameter greater than about 10 μm.

21. A process according to claim 20, wherein the step of collecting said microbubbles comprises separating said intermediate layer from said lower layer and said upper layer.

22. A process according to claim 15, further comprising an additional step of washing said microbubbles with a solvent.

23. A process according to claim 15, further comprising an additional step of cooling said mixture to a first temperature.

24. A process according to claim 15, wherein said first temperature is about 4° C.

25. A method for altering the contrast of an ultrasonic image, comprising the steps of:

forming a mixture of a solvent, a first surfactant and a second, dispersible surfactant, said second surfactant being different from said first surfactant, said mixture having stabilized gas microbubbles with a mean diameter of less than about 10 micrometers formed therein by sonication;

collecting said microbubbles by separating at least a portion of said solvent from said microbubbles; and injecting said microbubbles into a body, whereby said microbubbles are effective to substantially alter the contrast of an ultrasonic image of a portion of the body containing said microbubbles therein.

26. A method according to claim 25, further comprising the step of substantially evenly distributing said microbubbles within a saline solution prior to injecting said microbubbles into said body.

* * * * *